US010373530B2

(12) United States Patent
Nordquist et al.

(10) Patent No.: US 10,373,530 B2
(45) Date of Patent: Aug. 6, 2019

(54) INTRAVENOUS BAG AND LINE LABEL (71) Applicant: PharMEDium Services, LLC, Lake Forest, IL (US)

(72) Inventors: Jeffrey S. Nordquist, Lake Barrington, IL (US); Steven M. Maraone, Lake Zurich, IL (US); Daane E. Hoffman, Winthrop Harbor, IL (US)

(73) Assignee: PHARMEDIUM SERVICES, LLC, Lake Forest, IL (US)

( * ) Notice: Subject to any disclaimer, the term of this patent is extended or adjusted under 35 U.S.C. 154(b) by 0 days.

(21) Appl. No.: 16/053,091

(22) Filed: Aug. 2, 2018

(65) Prior Publication Data

US 2019/0035310 A1    Jan. 31, 2019

Related U.S. Application Data (60) Provisional application No. 62/539,199, filed on Jul. 31, 2017.

(51) Int. Cl.
| | |
|---|---|
| *G09F 3/10* | (2006.01) |
| *A61M 5/14* | (2006.01) |
| *A61J 1/10* | (2006.01) |
| *G09F 3/00* | (2006.01) |
| *G09F 3/02* | (2006.01) |

(52) U.S. Cl.
CPC ............... *G09F 3/10* (2013.01); *A61J 1/10* (2013.01); *A61M 5/14* (2013.01); *G09F 3/0295* (2013.01); *A61J 2205/30* (2013.01); *A61M 2205/60* (2013.01); *G09F 2003/0201* (2013.01); *G09F 2003/0222* (2013.01); *G09F 2003/0229* (2013.01); *G09F 2003/0269* (2013.01)

(58) Field of Classification Search
CPC .. G09F 3/10; G09F 3/0295; G09F 2003/0222; A61J 1/10; A61J 2205/30; A61M 5/14; A61M 2205/60
See application file for complete search history.

(56) References Cited

U.S. PATENT DOCUMENTS

| | | | |
|---|---|---|---|
| D687,894 S | 8/2013 | Langan et al. | |
| 8,597,271 B2 | 12/2013 | Langan et al. | |
| 8,808,249 B2 | 8/2014 | Langan et al. | |
| 2002/0056989 A1* | 5/2002 | Lewis-Leander | G09F 3/0288 283/81 |

(Continued)

*Primary Examiner* — Gary C Hoge
(74) *Attorney, Agent, or Firm* — Michael Best & Friedrich LLP (57) ABSTRACT

A label for use with an intravenous bag having a surface and an interior volume for holding a solution in fluid communication with an intravenous line for dispensing the solution, where the label includes a back layer including an adhesive for securing the label to a surface of the intravenous bag, a front layer with a solution name including a first portion secured to the back layer, the front layer including a second portion removable from the back layer engageable with the intravenous line with the solution name on a first side and a second side. In some constructions, the solution name on the second side is inverted with respect to the solution name on the first side, and the second portion further includes an opening for viewing a portion of the intravenous line when the second portion is engaged with the intravenous line.

12 Claims, 5 Drawing Sheets

(56) References Cited

U.S. PATENT DOCUMENTS

| | | | | |
|---|---|---|---|---|
| 2003/0214129 | A1* | 11/2003 | Adler | A61J 7/04 |
| | | | | 283/81 |
| 2006/0196951 | A1* | 9/2006 | Lowmaster | A61J 1/1406 |
| | | | | 235/494 |
| 2009/0143745 | A1* | 6/2009 | Langan | G09F 3/0288 |
| | | | | 604/189 |
| 2013/0289496 | A1* | 10/2013 | Langan | A61M 5/1417 |
| | | | | 604/257 |
| 2014/0237873 | A1* | 8/2014 | Garay-Marrero | G09F 3/02 |
| | | | | 40/674 |
| 2015/0272828 | A1* | 10/2015 | Pfanner | G06Q 50/22 |
| | | | | 604/404 |
| 2018/0036310 | A1* | 2/2018 | Kumar | A61K 31/519 |
| 2018/0168931 | A1* | 6/2018 | Williams | C09J 7/38 |
| 2018/0225999 | A1* | 8/2018 | Raming | G09F 3/10 |

* cited by examiner

INTRAVENOUS BAG AND LINE LABEL

BACKGROUND

The present disclosure relates to a system for ensuring accuracy of printed labels for intravenous bags and for intravenous lines engaged with the intravenous bags.

In the healthcare industry, solutions, such as diluent solutions, such as saline solutions or dextrose solutions, or solutions including pharmaceutical compounds, such as compounded drugs, may be administered to a patient intravenously. A solution to be administered intravenously is packaged within an intravenous bag and dispensed to the patient through an intravenous line engaged with the intravenous bag.

Intravenous bags are typically labeled with information identifying a name of the solution, for example a name of the diluent or a name of the pharmaceutical compound in the solution. Color-coded labels, color-coded risk indicators, and TALLman letters are often used to assist healthcare professionals in quickly and accurately identifying the solution dispensed from each of the intravenous bags.

A patient may be simultaneously treated with multiple intravenously-delivered solutions. Each solution is delivered from an intravenous bag through a dedicated intravenous line. The intravenous lines engaged with the intravenous bags are often also labeled with the name of the solution to avoid confusion between lines from different bags, for example when changing intravenous bags or inspecting intravenous lines. However, the intravenous line labels are typically provided separately from the intravenous bag labels, which could lead to mislabeling of the intravenous line. Furthermore, the intravenous line label may block the labeled portion of the intravenous line, preventing a healthcare provider from noticing air bubbles, discoloration, blockages, or other abnormalities present in the labeled portion of the intravenous line.

SUMMARY

The present disclosure relates to a labeling system that reduces the likelihood of label printing errors and mismatched intravenous bag and intravenous line labels. The labeling system of the present disclosure provides a label in which a bag label portion and a line label portion are printed onto a shared backing. The bag label portion is fixed to the shared backing and the line label portion is removably attached to the shared backing, enabling the line label to be removed from the liner and secured to an intravenous bag as a single unit. The removable intravenous line label may also include an opening that allows visualization of the labeled portion of the intravenous line. This opening enables a healthcare provider to inspect the labeled intravenous line at the point of attachment of the line label for air bubbles, discoloration, blockages, or other issues in the fluid flowing through the labeled portion of the intravenous line.

In one construction, the disclosure provides a label for use with an intravenous bag having a surface and an interior volume for holding a solution. The intravenous bag is in fluid communication with an intravenous line for dispensing the solution. The label includes a back layer including an adhesive for securing the label to a surface of the intravenous bag. The label further includes a front layer including a first portion secured to the back layer and including a solution name. The front label in turn includes a second portion removable from the back layer and engageable with the intravenous line. The second portion includes the solution name on a first side and a second side. The solution name on the second side is inverted with respect to the solution name on the first side. The second portion may also include an opening for viewing a portion of the intravenous line when the second portion is engaged with the intravenous line. In another construction, the solution name on the second side is not inverted with respect to the solution name on the first side.

In another construction, the disclosure provides an intravenous solution delivery system including an intravenous bag having a surface and an interior volume adapted to receive a solution. The intravenous solution delivery system also includes an intravenous line engaged with the intravenous bag for dispensing the solution. The intravenous solution delivery system further includes a label attached to the intravenous bag. The label includes a back layer having an adhesive for securing the label to a surface of the intravenous bag. The label further includes a front layer including a first portion secured to the back layer and including a solution name. The front layer further includes a second portion removable from the back layer and engageable with the intravenous line. The second portion includes the solution name on a first side and a second side. The solution name on the second side is inverted with respect to the solution name on the first side. The second portion may also include an opening for viewing a portion of the intravenous line when the second portion is engaged with the intravenous line. In another construction, the solution name on the second side is not inverted with respect to the solution name on the first side.

In another construction, the disclosure provides a method of labeling an intravenous line engaged with an intravenous bag including a surface and defining an interior volume for receiving a solution. The method includes providing a label including a back layer including an adhesive for securing the label to a surface of the intravenous bag a front layer including a first portion secured to the back layer and including a solution name. The front layer further includes a second portion removable from the back layer and engageable with the intravenous line. The second portion has the solution name on a first side and a second side. The solution name on the second side is inverted with respect to the solution name on the first side. The second portion may also include an opening for viewing a portion of the intravenous line when the second portion is engaged with the intravenous line. The method further includes engaging the label with the surface of the intravenous bag; detaching the second portion of the label from the first portion of the label; aligning the opening of the second portion along the intravenous line; and folding the second portion about the intravenous line to secure the second side to the first side so that the first side and the second side display the name of the solution.

In another construction, the disclosure provides a method of printing an intravenous bag label for use with an intravenous bag engageable with an intravenous line. The method includes selecting a solution name from a solution information database stored in a memory of a label printer. In response to selecting the solution name, the method further includes retrieving printing instructions from the solution information database. The printing instructions include a type of a roll of labels upon which to print the solution name. The method further includes aligning the roll of labels with a printing member of the label printer. The roll of labels includes a backing sheet having a machine-readable label including a type of the roll of labels. The method further includes scanning the machine-readable label on the roll of labels to confirm the type of the roll of labels. The method further includes printing at least one label of the roll of labels according to the printing instructions.

Other aspects of the disclosure will become apparent by consideration of the detailed description and accompanying drawings.

DETAILED DESCRIPTION

Before any constructions of the disclosure are explained in detail, it is to be understood that the disclosure is not limited in its application to the details of construction and the arrangement of components set forth in the following description or illustrated in the following drawings. The disclosure is capable of other constructions and of being practiced or of being carried out in various ways. In any disclosed construction, the term "approximately" may be substituted with "within a percentage of" what is specified, wherein the percentage includes 0.1, 1, 5, and 10 percent.

Figure 1:
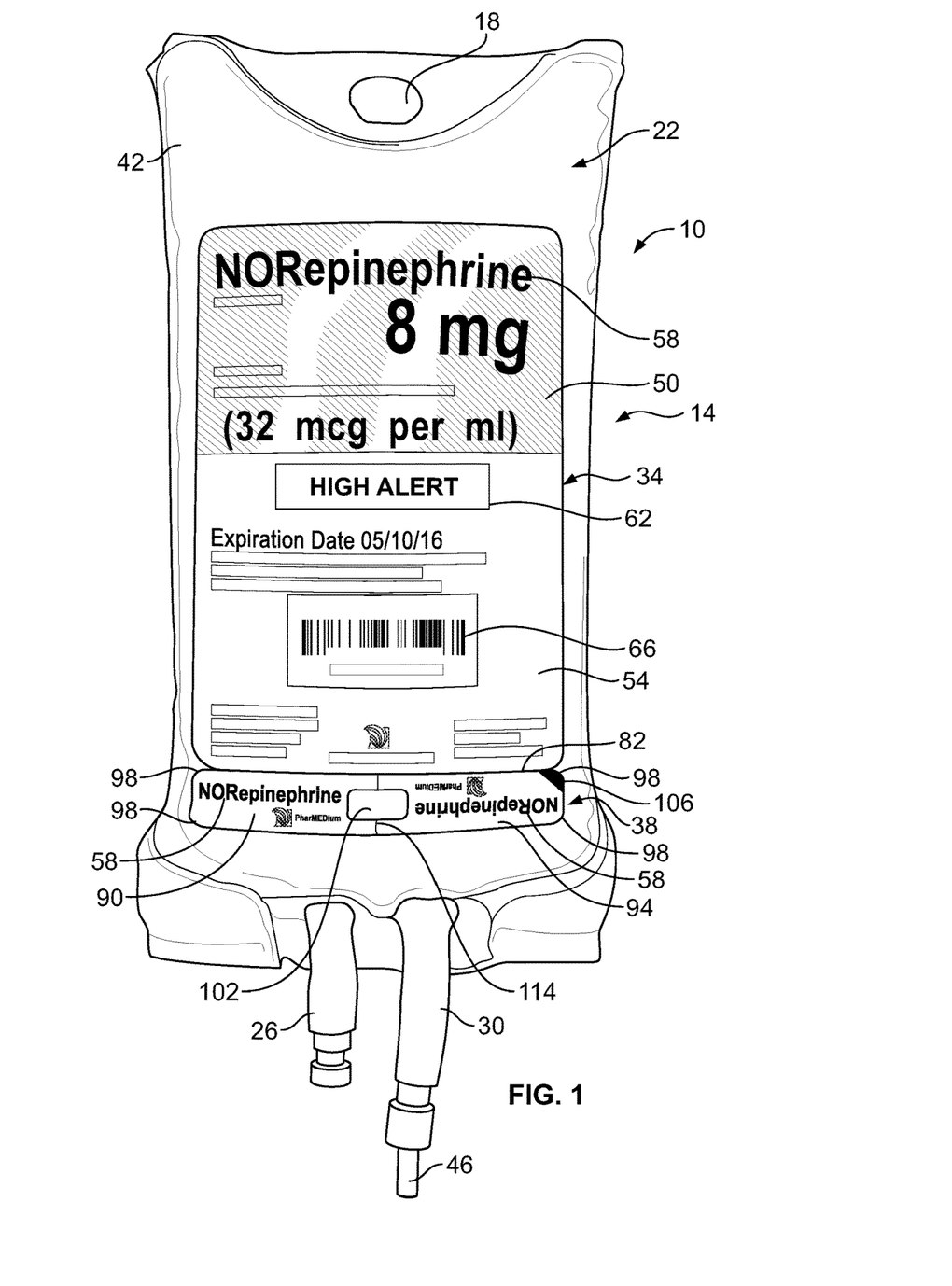
FIG. 1 is a perspective view of an intravenous bag labeling system engaged with an intravenous bag.

FIG. 1 illustrates an intravenous bag 10 that includes an intravenous bag label 14, a hanger hole 18, an internal volume 22, a medication port 26, and an intravenous line port 30. The intravenous bag label 14 includes a bag label 34 and a line label 38. In the illustrated construction, the intravenous bag label 14 is mounted on a front face 42 of the intravenous bag 10. A similar or identical label may be attached to the back face (not shown) of the intravenous bag 10. The hanger hole 18 is positioned proximate a top of the intravenous bag 10 for mounting the intravenous bag 10 on an intravenous bag pole (not shown). The internal volume 22 receives a solution for administration to a patient. The medication port 26 is positioned proximate a bottom of the intravenous bag 10. The medication port 26 allows a healthcare provider to add medication to the solution inside the internal volume 22. The intravenous line port 30 is positioned proximate the bottom of the intravenous bag 10. The intravenous line port 30 receives an intravenous line 46 for administering the solution to the patient.

Figure 2:
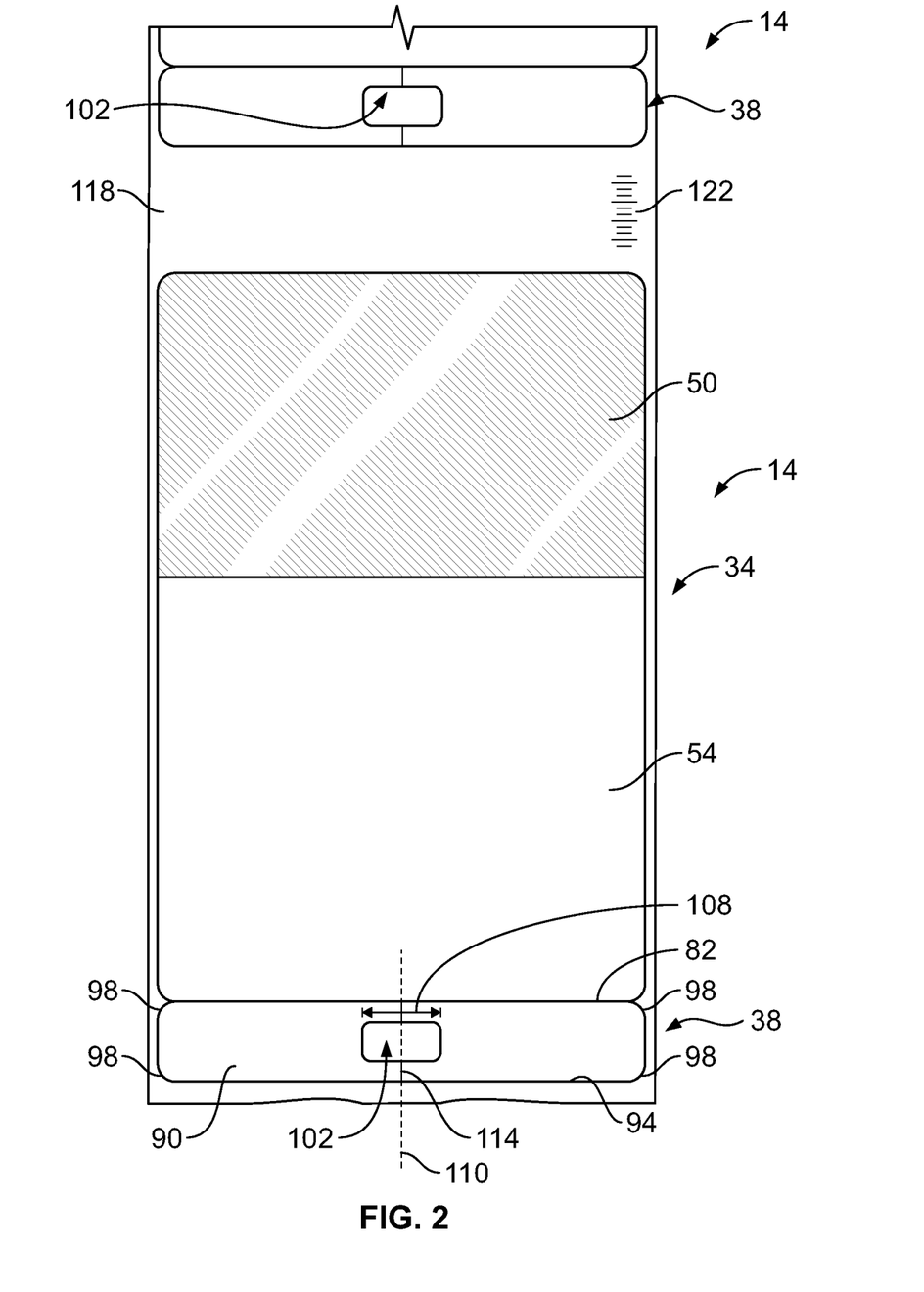
FIG. 2 is a view of a portion of a roll of intravenous bag labels that includes the intravenous bag labels of FIG. 1 before printing according to one construction.

As shown in FIGS. 1 and 2, the bag label 34 may include an upper portion 50 and a lower portion 54. The upper portion 50 of the bag label 34 and/or the intravenous line label 38 may be color-coded to assist a user in identifying the solution stored in the intravenous bag 10. The upper portion 50 may also include information such as a name 58 of the solution, a total dose of the solution, or a concentration of the solution, and a total volume of the solution. The lower portion 54 may include a risk indicator 62 to alert a user to a risk characteristic of the drug, such as the "high alert" indicator 62 shown positioned beneath the upper portion 50 in FIG. 1. The label lower portion 54 may also include identifying information such as a lot number of the solution, a packaging date of the solution, and an expiration date of the solution. The lower portion 54 may also include a machine-readable label 66 that includes identifying information about the solution stored in the intravenous bag 10. Exemplary identifying information may include the name 58 of the solution, the dose or the composition of the solution, the total volume of the solution, the lot number of the solution, the expiration date of the solution, and/or the packing date of the solution. In the construction illustrated in FIG. 1, the machine-readable label 66 is a barcode. In other constructions, the machine-readable label 66 may be an RFID tag embedded in the intravenous bag label 14. In some constructions, the intravenous bag label 14 may be made from a material that may be written-upon by a user.

Figure 3:
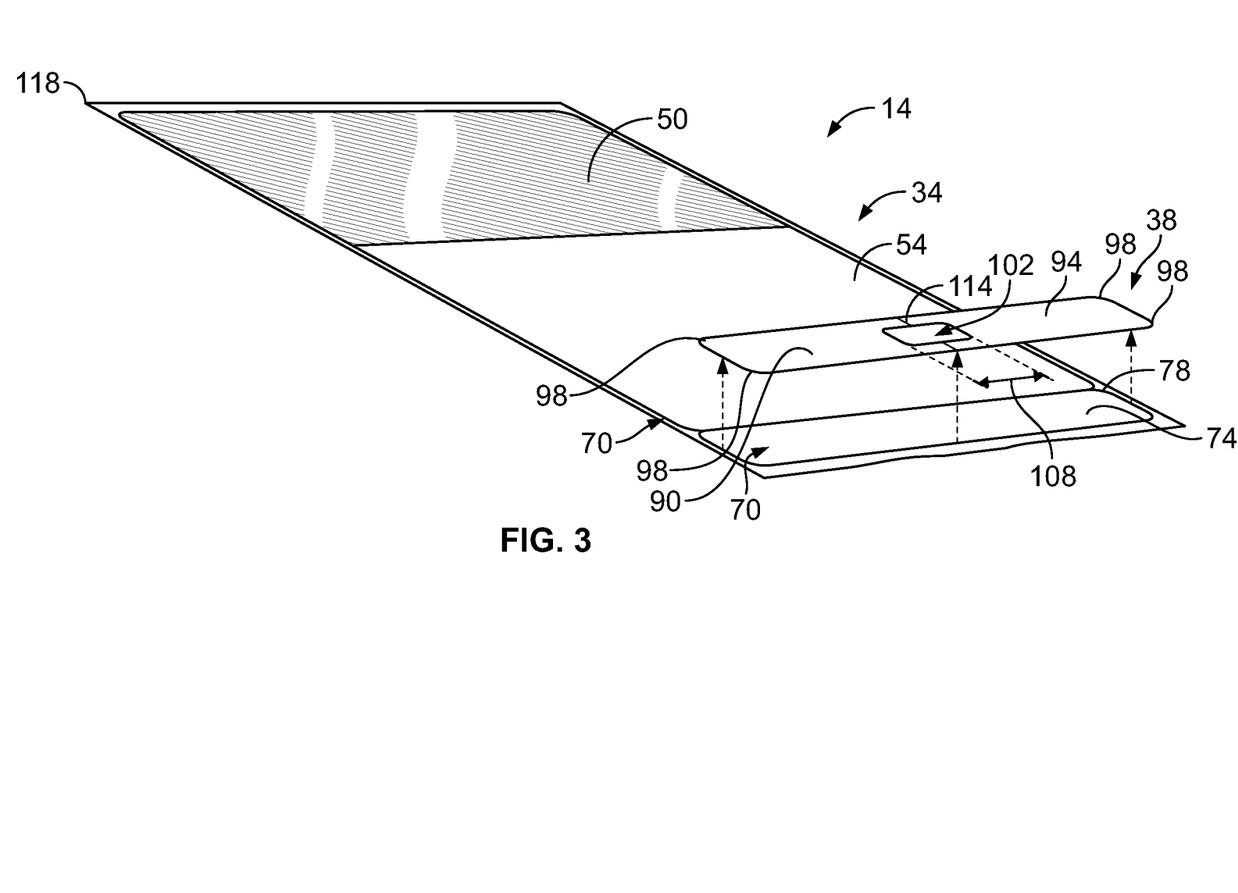
FIG. 3 is an exploded view of the intravenous bag label of FIG. 2.

As illustrated in FIG. 3, the bag label 34 is attached to a carrier sheet 70. The carrier sheet 70 is affixed to the front face 42 of the intravenous bag 10 with an adhesive (not shown) that ensures that the carrier sheet 70 cannot easily be removed from the intravenous bag 10 (FIG. 1). The carrier sheet 70 is longer than the bag label 34. Since the carrier sheet 70 is longer than the bag label 34, a portion 74 of the carrier sheet 70 extends beyond an end 78 of the bag label 34. The line label 38 may be attached to the portion 74 of the carrier sheet 70 that extends beyond the end 78 of the bag label 34. The line label 38 may be removed from the portion 74 of the carrier sheet 70 without disturbing the bag label 34 when the intravenous bag labeling system 14 is secured to the intravenous bag 10. In the illustrated construction, the bag label 34 and the line label 38 may be separated by a slit 82. The line label 38 may include a marking 106 (FIGS. 4-5) proximate the slit 82 to encourage a user to remove the line label 38 from the bag label 34. In other constructions, the bag label 34 and the line label 38 are separated by a perforated line. To facilitate removal of the line label 38, in some constructions, at least some of the portion 74 of the carrier sheet 70 that extends beyond the end 78 of the bag label 34 may include a non-stick coating. In some constructions, the entire portion 74 includes a non-stick coating.

Figure 4:
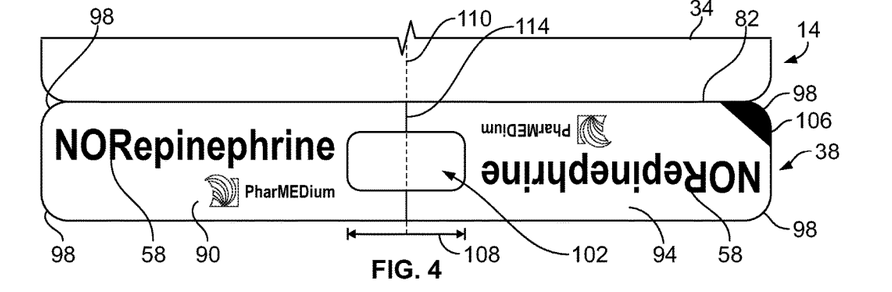
FIG. 4 is a detail view of a line label portion of the intravenous bag label of FIG. 2 according to one construction.
Figure 5:
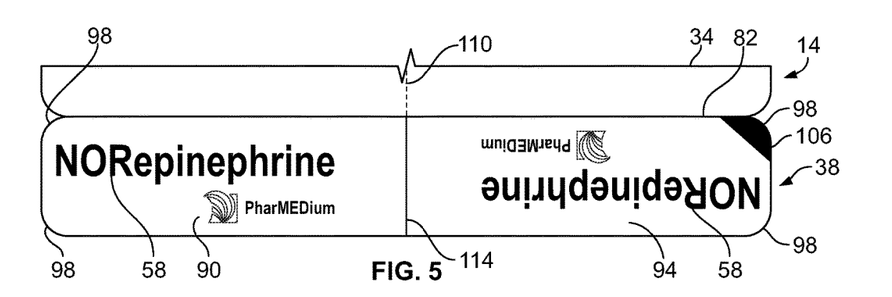
FIG. 5 is a detail view of a line label portion of the intravenous bag label of FIG. 2 according to another construction.
Figure 6:
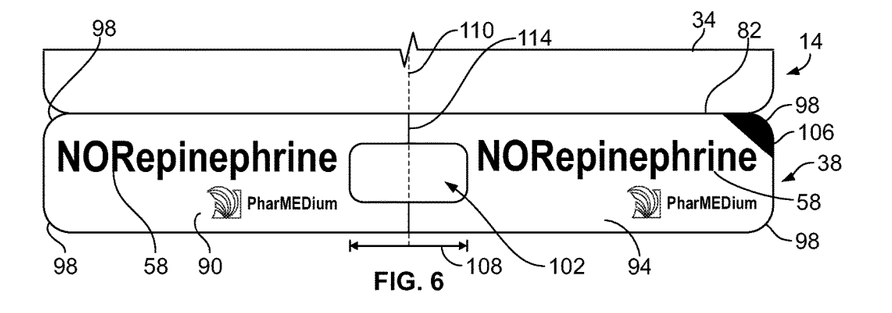
FIG. 6 is a detail view of a line label portion the intravenous bag label of FIG. 2 according to another construction.

As is best shown in FIGS. 4-6, the line label 38 includes a first portion 90 and a second portion 94. The name 58 of the solution stored in the internal volume 22 of the intravenous bag 10 is printed on the front of the first portion 90 and the front of the second portion 94. In the construction illustrated in FIGS. 4 and 5, the name 58 printed on the second portion 94 is inverted with respect to the name 58 printed on the first portion 90. The name 58 of the solution is therefore readable by a user from above or below the line label 38 when the line label 38 is engaged with the intravenous line 46. In some constructions, such as shown in FIG. 6, the name 58 printed on the second portion 94 is not inverted with respect to the name 58 printed on the first portion 90. At least a portion of the back of the first portion 90 or the back of the second portion 94 of the line label 38 includes an adhesive (not shown). When the line label 38 is secured to the intravenous line 46 (FIG. 8), the adhesive secures the back of the first portion 90 to the back of the second portion 94. A portion of the adhesive may engage the intravenous line 46 to reduce slipping of the line label 38 along the intravenous line 46. As is best shown in FIGS. 4-8, the removable line label 38 has rounded corners 98 to reduce possible patient discomfort should the label rub against a patient when the line label 38 is engaged with the intravenous line 46. In the illustrated construction, the rounded corners 98 of the line label 38 are formed by die-cutting. In some constructions, a central axis 110 of the opening 102 shown with a line 114 positioned to assist a user in aligning the line label 38 with the intravenous line 46. The line label 38 may be removed from the intravenous line 46. For example, a healthcare practitioner may tear the line label 38 off of the intravenous line 46 after the patient has stopped being treated with the solution in the intravenous bag 10.

In some constructions, such as the constructions of FIGS. 4 and 6-8, the line label 38 may include an opening 102. The opening 102 preferably has a width 108 longer than a circumference of the intravenous line 46. The intravenous line 46 is therefore visible when the line label 38 is engaged with the intravenous line 46. The opening 102 allows the user to check for air bubbles, discoloration, or any other abnormalities in the intravenous line 46 while the line label 38 is engaged with the intravenous line 46. As shown in FIG. 4, the opening 102 may be substantially centered along the line label 38. In other constructions, the opening 102 may be off-center along the line label 38. In the illustrated construction, the opening 102 is formed by die-cutting.

Referring again to FIG. 2, the unitary construction of the intravenous bag label 14 enables the line label 38 to be printed at the same time as the bag label 34 is printed, which reduces the likelihood that the intravenous line 46 could be mislabeled. In constructions in which the intravenous bag label 14 is printed using a label printing machine 126, intravenous bag labels 14 that have not yet been printed with the solution name 58 may be provided on a backing sheet 118. The backing sheet 118 may be rolled into a spool of unprinted intravenous bag labels 14. The intravenous bag labels 14 may include color coding on the upper portion 50, the lower portion 54, and/or the risk indicator 62 printed on the lower portion 54. The backing sheet 118 of each roll may include a machine-readable label 122 (FIG. 2) that includes data about any color coding or indicia pre-printed on the intravenous bag labels 14. In the illustrated construction, the machine-readable label 122 is generally perpendicular to a longitudinal extent of the backing sheet 118 and offset from a center of a width of the backing sheet 118. In the illustrated construction, the machine-readable label 122 is printed on a front side (e.g. the side including the intravenous bag labels 14) of the backing sheet 118. In other constructions, the machine-readable label may be printed on a back side of the backing sheet 118. In the illustrated construction, the machine-readable label 122 is a barcode including a roll stock number of the roll of intravenous bag labels 14. The rolls of intravenous bag labels 14 may be used with the label printing machine 126.

Figure 9:
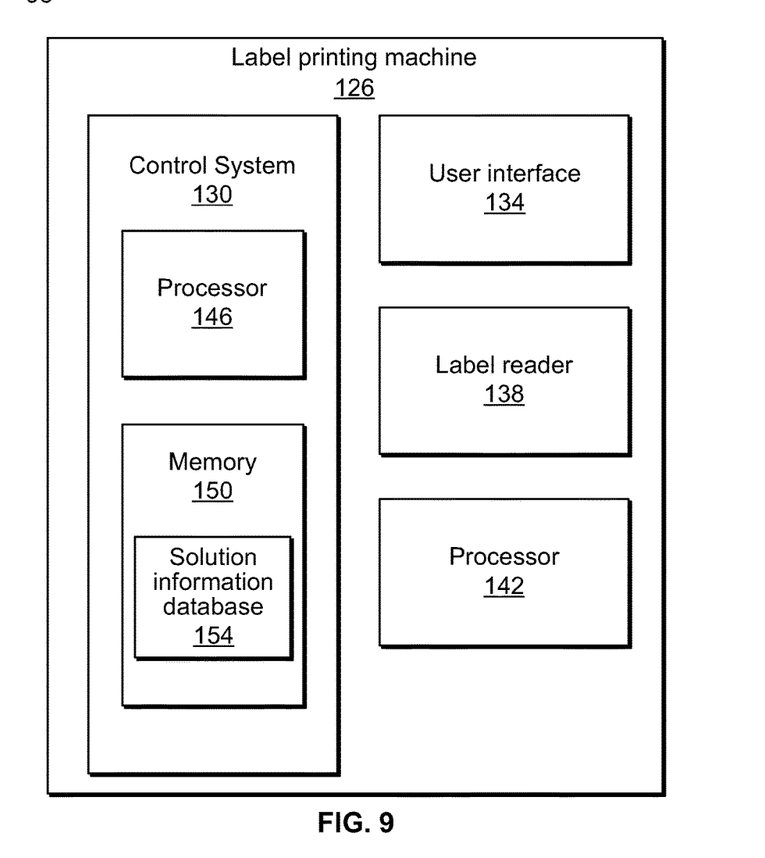
FIG. 9 is a schematic representation of a printing machine for printing the intravenous bag label of FIG. 2 according to some constructions.

With reference to FIG. 9, the label printing machine 126 includes a control system 130, a user interface 134, a label reader 138, and a printer 142. In some constructions, the control system 130 is included the label printing machine 126. In other constructions, the control system may be included in a computing device that is in electronic communication with the label printing machine. The control system 130 includes a processor 146 and a memory 150. The memory 150 includes a solution information database 154.

The solution information database 154 includes information that must be printed on the intravenous bag labels 14 for each solution that could be stored in and dispensed from the intravenous bag 10. For example, the solution information database 154 may include information such as the name 58 of the drug or solution, the dose or the composition of the solution, the total volume of the solution, the expiration date of the solution, the lot number of the solution, and any other information required by labelling standards. The solution information database 154 may also include label printing instructions that may specify a specific color code or risk indicator 62 that must be included on the intravenous bag labels 14. In the illustrated construction, the label printing machine 126 is adapted to receive preprinted rolls of intravenous bag labels 14 that include color coding and alert indicia. The label printing machine 126 may also receive rolls of intravenous bag labels 14 that are not pre-printed with color coding or risk indicators 62.

In operation, a user verifies the solution name 58 for printing onto the intravenous bag label 14 or to print onto multiple intravenous bag labels 14. The user enters the solution name 58 into user interface 134 of the label printing machine 126, for example by scanning a machine-readable label including the solution name 58 and the barcode roll stock number 14 with the label reader 138 of the label printing machine 126. In response to receiving the solution name 58, the control system 130 retrieves the information that must be printed onto the intravenous bag label 14 from the solution information database 154. The label reader 138 then reads the machine-readable label 122 printed on the backing sheet 118 to ensure that the correct roll of intravenous bag labels 14 has been aligned with the printer 142. The machine-readable label 122 may also be scanned with a manual label reader (not shown) and a user may manually verify that the correct roll of intravenous bag labels 14 is being used. The printer 142 then prints the drug information onto the intravenous bag labels 14. In some constructions, the label reader 138 periodically checks the machine-readable label 122 printed on the backing sheet 118 to verify that the correct roll of intravenous bag labels 14 is being is used. Since the bag label 34 and the line label 38 are formed of a unitary intravenous bag label 14, both the bag label 34 and the line label 38 are printed at the same time. Accordingly, both the bag label 34 and the line label 38 include the name 58 of the same solution. In some constructions, the bag label 34 and the line label 38 may include other identifying information about the solution.

In operation, the intravenous bag label 14 is removed from the backing sheet 118 (e.g. on a spool or on a sheet of labels) as a single unit. The intravenous bag label 14 is then secured to the face 42 of the intravenous bag 10. In some constructions, the intravenous bag 10 has been filled with the same solution name as the solution name 58 printed on the intravenous bag label 14. In other constructions, the intravenous bag 10 will be filled with the same solution as the solution name 58 printed on the intravenous bag label 14. The internal volume 22 is then filled with the intravenous bag 10 with the solution that is printed on the intravenous bag label 14. The filled and labeled intravenous bag 10 is bagged for transportation to an end user, such as a healthcare worker. In some constructions, a second intravenous line label 14 may be secured to the intravenous bag 10, for example at a face on an opposite side of the intravenous bag 10 than the face 45.

Figure 7:
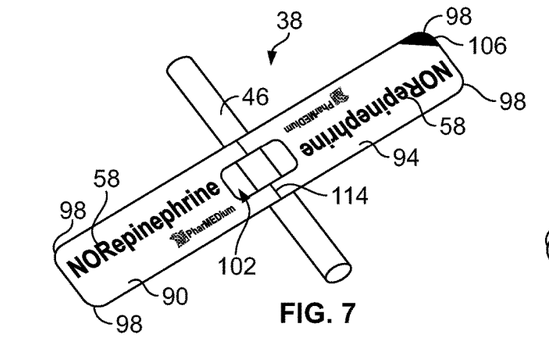
FIG. 7 is a perspective view of an intravenous line portion of the intravenous bag label of FIG. 2 aligned with an intravenous line.
Figure 8:
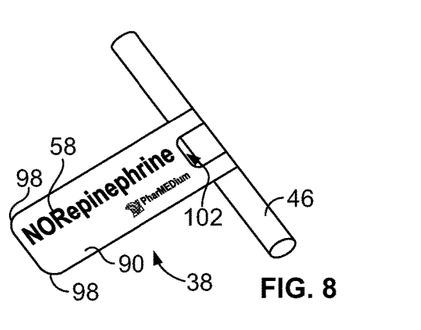
FIG. 8 is a perspective view of an intravenous line portion of the intravenous bag label of FIG. 2 engaged with an intravenous line.

When the intravenous bag 10 is deployed by a healthcare worker for use with a patient, the healthcare worker secures an end of intravenous line 46 to the intravenous bag 10. The healthcare worker then detaches the line label 38 from the bag label 34 by peeling the line label 38 away from the carrier sheet 70 along the slit 82. The healthcare worker then aligns the central axis 110 of the line label 38 with the intravenous line 46 as is shown in FIG. 7. In constructions in which two intravenous line labels 14 are secured to the intravenous bag 10, the healthcare worker may position one of the intravenous bag labels 14 on a portion of the intravenous line 46 that is proximate the intravenous bag 10 and one of the intravenous bag labels 14 on a portion of the intravenous line 46 that is (or will be) proximate the patient. The healthcare worker then folds the line label 38 about the intravenous line 46 so that the adhesive secures the back surface of the first portion 90 to the back surface of the second portion 94 to secure the line label 38 to the intravenous line 46. When the line label 38 is secured to the intravenous line 46, the line label 38 displays the name 58 of the solution on the intravenous line 46. In constructions having the opening 102, the healthcare worker may inspect the intravenous line 46 through the opening 102. In constructions in which the intravenous bag label 14 is made by a material that may be written upon, the healthcare worker may write upon on the intravenous bag label 14. For example, the healthcare worker may write a date and a time at which the intravenous treatment started upon the intravenous bag label 14.

Various features and advantages of the disclosure are set forth in the following claims.

What is claimed is:

1. A label for use with an intravenous bag having a surface and an interior volume for holding a solution in fluid communication with an intravenous line for dispensing the solution, the label comprising:
    a back layer including an adhesive for securing the label to a surface of the intravenous bag; and
    a front layer including:
        a first portion secured to the back layer displaying a solution name, and
        a second portion removable from the back layer and engageable with the intravenous line, the second portion including the solution name on a first side and a second side, the solution name on the second side inverted with respect to the solution name on the first side, and an opening for viewing a portion of the intravenous line when the second portion is engaged with the intravenous line.

2. The label of claim 1, wherein the second portion is foldable about the intravenous line to secure the second portion to the intravenous line and wherein the first side and the second side display the solution name when the second portion is engaged with the intravenous line.

3. The label of claim 1, wherein at least a portion of a back of the second portion has an adhesive proximate the opening.

4. The label of claim 1, wherein the second portion has rounded corners.

5. The label of claim 1, wherein the opening has a width that is larger than a circumference of the intravenous line.

6. The intravenous solution delivery system of claim 5, wherein a portion of the intravenous line is visible through the opening when the second portion is positioned along the intravenous line.

7. The label of claim 1, wherein a slit is formed between the first portion and the second portion.

8. An intravenous solution delivery system comprising:
    an intravenous bag including a surface and an interior volume adapted to receive a solution;
    an intravenous line engaged with the intravenous bag and configured to dispense the solution;
    a label attached to the intravenous bag, the label including:
        a back layer including an adhesive for securing the label to a surface of the intravenous bag; and
        a front layer including:
            a first portion secured to the back layer and including a solution name, and
            a second portion removable from the back layer and engageable with the intravenous line, the second portion including the solution name on a first side and a second side, the solution name on the second side inverted with respect to the solution name on the first side, and an opening for viewing a portion of the intravenous line when the second portion is engaged with the intravenous line.

9. The intravenous solution delivery system of claim 8, wherein the second portion is foldable about the intravenous line to secure the second portion to the intravenous line and the first side and the second side display the name of the solution when the second portion is engaged with the intravenous line.

10. The intravenous solution delivery system of claim 8, wherein a width of the opening is larger than a circumference of the intravenous line.

11. The intravenous solution delivery system of claim 10, wherein a portion of the intravenous line is visible through the opening when the second portion is positioned along the intravenous line.

12. The intravenous solution delivery system of claim 8, wherein a perforated line is formed between the first portion and the second portion.

* * * * *